US009046472B2

(12) United States Patent
Man et al.

(10) Patent No.: US 9,046,472 B2
(45) Date of Patent: Jun. 2, 2015

(54) CRYSTAL ANALYSIS APPARATUS, COMPOSITE CHARGED PARTICLE BEAM DEVICE, AND CRYSTAL ANALYSIS METHOD

(71) Applicant: Hitachi High-Tech Science Corporation, Tokyo (JP)

(72) Inventors: Xin Man, Tokyo (JP); Toshiaki Fujii, Tokyo (JP)

(73) Assignee: HITACHI HIGH-TECH SCIENCE CORPORATION (JP)

( * ) Notice: Subject to any disclaimer, the term of this patent is extended or adjusted under 35 U.S.C. 154(b) by 81 days.

(21) Appl. No.: 14/025,985

(22) Filed: Sep. 13, 2013

(65) Prior Publication Data

US 2014/0077097 A1 Mar. 20, 2014

(30) Foreign Application Priority Data

Sep. 18, 2012 (JP) .................................. 2012-204612

(51) Int. Cl.
*H01J 37/28* (2006.01)
*G01N 23/203* (2006.01)
(52) U.S. Cl.
CPC .................................... *G01N 23/203* (2013.01)

(58) Field of Classification Search
USPC .............. 250/306, 307, 309, 310, 311, 491.1, 250/492.1, 492.21, 492.3; 702/150–153, 702/159; 264/1.36
See application file for complete search history.

(56) References Cited

U.S. PATENT DOCUMENTS

| 8,803,111 | B2 * | 8/2014 | Man .......................... 250/492.22 |
| 2005/0103995 | A1 * | 5/2005 | Yanagiuchi et al. .......... 250/309 |
| 2011/0186734 | A1 * | 8/2011 | Hasuda et al. ................. 250/307 |
| 2013/0241091 | A1 * | 9/2013 | Man .............................. 264/1.36 |

FOREIGN PATENT DOCUMENTS

JP 2011159483 8/2011

* cited by examiner

*Primary Examiner* — Bernard E Souw
(74) *Attorney, Agent, or Firm* — Adams & Wilks

(57) ABSTRACT

A crystal analysis apparatus includes: a measurement data storage configured to store electron back-scattering pattern (EBSP) data measured at electron beam irradiation points on a plurality of cross-sections of a sample formed substantially in parallel at prescribed intervals; a crystal orientation database configured to accumulate therein information of crystal orientations corresponding to EBSPs; and a map constructing unit that constructs a three-dimensional crystal orientation map based on distribution of crystal orientations in normal directions of a plurality of faces of a polyhedral image having the cross-sections arranged at the prescribed intervals by reading out the crystal orientations in the normal directions of the faces from the crystal orientation database on the basis of the EBSP data stored in the measurement data storage.

10 Claims, 6 Drawing Sheets

CRYSTAL ANALYSIS APPARATUS, COMPOSITE CHARGED PARTICLE BEAM DEVICE, AND CRYSTAL ANALYSIS METHOD

CROSS-REFERENCE TO RELATED APPLICATIONS

The present application claims priority from Japanese Patent Application No. 2012-204612 filed on Sep. 18, 2012, the entire-subject matter of which is incorporated herein by reference.

BACKGROUND

1. Technical Field

The present invention relates to a crystal analysis apparatus for performing crystal analysis on information of backscattered electrons acquired from a sample through electron beam irradiation.

2. Related Art

There has been known an electron scanning microscope which performs crystal analysis of a sample through measurement of an electron back-scattering pattern (EBSP) by irradiating the sample with electron beams (EB) and detecting electrons backscattered by the sample. Recent apparatuses include a crystal analysis apparatus that forms cross-sections of a sample by focused ion beams (FIB) and measures EBSPs of the cross-sections serially to construct a three-dimensional (3D) crystal orientation map of the sample (see JP-A-2011-159483).

SUMMARY

The above-described related-art apparatus have some disadvantages. For example, the related-art apparatus constructs a 3D crystal orientation map by stacking two-dimensional (2D) crystal orientation maps of cross-sections formed by FIB. Crystal orientations are therefore accurately displayed only on the cross-sections but not on the side surfaces of the 3D crystal orientation map.

Therefore, illustrative aspects of the present invention provide a crystal analysis apparatus capable of constructing a 3D crystal orientation map displaying crystal orientations appropriate to the faces of a polyhedral image of a sample.

(1) According to one illustrative aspect of the present invention, there is provided a crystal analysis apparatus including: a measurement data storage configured to store EBSP data measured at electron beam irradiation points on a plurality of cross-sections of a sample formed substantially in parallel at prescribed intervals; a crystal orientation database configured to accumulate therein information of crystal orientations corresponding to EBSPs; and a map constructing unit configured to construct a three-dimensional crystal orientation map based on distribution of crystal orientations in the normal directions of a plurality of faces of a polyhedral image having the cross-sections arranged at the prescribed intervals by reading out the crystal orientations in the normal directions of the faces from the crystal orientation database on the basis of the EBSP data stored in the measurement data storage.

The polyhedral image is, for example, a hexahedral image. A display direction is set to display desired, one or more faces of the hexahedral image.

The apparatus reads out information of crystal orientations of the side surfaces of a polyhedral image in the normal directions of the side surfaces, which are faces other than cross-sections formed by FIB, from the crystal orientation database to construct a 3D crystal orientation map on the basis of measured EBSP data. This allows the faces of the polyhedral image to display crystal orientations in the normal directions of the faces. Correct crystal orientations are therefore displayed on the side surfaces in the 3D crystal orientation map. The 3D crystal orientation map can also be constructed for exposed internal faces obtained by cutting the polyhedral image. The internal faces may be tilted with respect to the side surfaces of the polyhedral image.

The crystal analysis apparatus according to the present invention may construct a 3D crystal orientation map when the faces include a plurality of crystal grains with different crystal orientations. Being analyzed on the basis of EBSP data measured at irradiation points on cross-sections, crystal orientations can be displayed for crystal faces of the crystal grains with different crystal orientations within the single face.

The map constructing unit included in the crystal analysis apparatus according to the present invention may include: a first map constructing unit that constructs a 2D crystal orientation map based on distribution of crystal orientations in the normal direction of a first face of the polyhedral image; and a second map constructing unit that constructs a 2D crystal orientation map based on distribution of crystal orientations in the normal direction of a second face adjacent to the first face. The map constructing unit may further include an input unit that designates a display direction of the three-dimensional crystal orientation map.

For a polyhedral image displayed in a display direction designated by the input unit, the above configuration enables simultaneous display of a 2D crystal orientation map based on distribution of crystal orientations in the normal direction of a first face displayed on a display unit and a 2D crystal orientation map based on distribution of crystal orientations in the normal direction of a second face adjacent to the first face. The display unit therefore displays a 3D crystal orientation map having correct crystal orientations in a desired display direction.

(2) According to another illustrative aspect of the invention, there is provided a composite charged particle beam apparatus including: the crystal analysis apparatus according to the above illustrative aspect; an FIB column configured to emit FIBs to form the cross-sections; an electron beam column configured to irradiate the cross-sections with an electron beam; and an EBSP detector configured to detect an EBSP at an EB irradiation point on the cross-sections.

The composite charged particle beam apparatus as a single apparatus forms a cross-section by FIB and detects an EBSP of the cross-section serially, thereby effectively performing crystal analysis of the cross-section.

(3) According to still another illustrative aspect of the present invention, there is provided a crystal analysis method including: forming a cross-section on a sample by irradiating the sample with a focused ion beam; detecting an electron back-scattering pattern (EBSP) at an electron beam irradiation point on the cross-section by irradiating the cross-section with an electron beam, the forming and the detecting being repeated to acquire EBSPs of a plurality of cross-sections arranged substantially in parallel at prescribed intervals to perform crystal analysis of the sample; and constructing a three-dimensional crystal orientation map based on distribution of crystal orientations that has crystal orientations in normal directions of a plurality of faces of a polyhedral image having the cross-sections arranged at the prescribed intervals as crystal orientations in the normal directions of the faces on the basis of the EBSP data.

The constructing of a three-dimensional crystal orientation map in the crystal analysis method according to the present invention may include: constructing a two-dimensional distribution of crystal orientations in a normal direction of a first face of the polyhedral image; and constructing a two-dimensional distribution of crystal orientations in a normal direction of a second face adjacent to the first face.

The crystal analysis method according to the present invention may further include: designating a display direction of the three-dimensional crystal orientation map; and displaying the three-dimensional crystal orientation map in the designated display direction.

The crystal analysis apparatus according to the present invention enables constructing a 3D crystal orientation map displaying crystal orientations in the normal directions of a plurality of faces of a polyhedral image of a sample on the basis of EBSP data of cross-sections formed in the sample.

DETAILED DESCRIPTION

Exemplary embodiments of the present invention will now be described with reference to the drawings.

Figure 1:
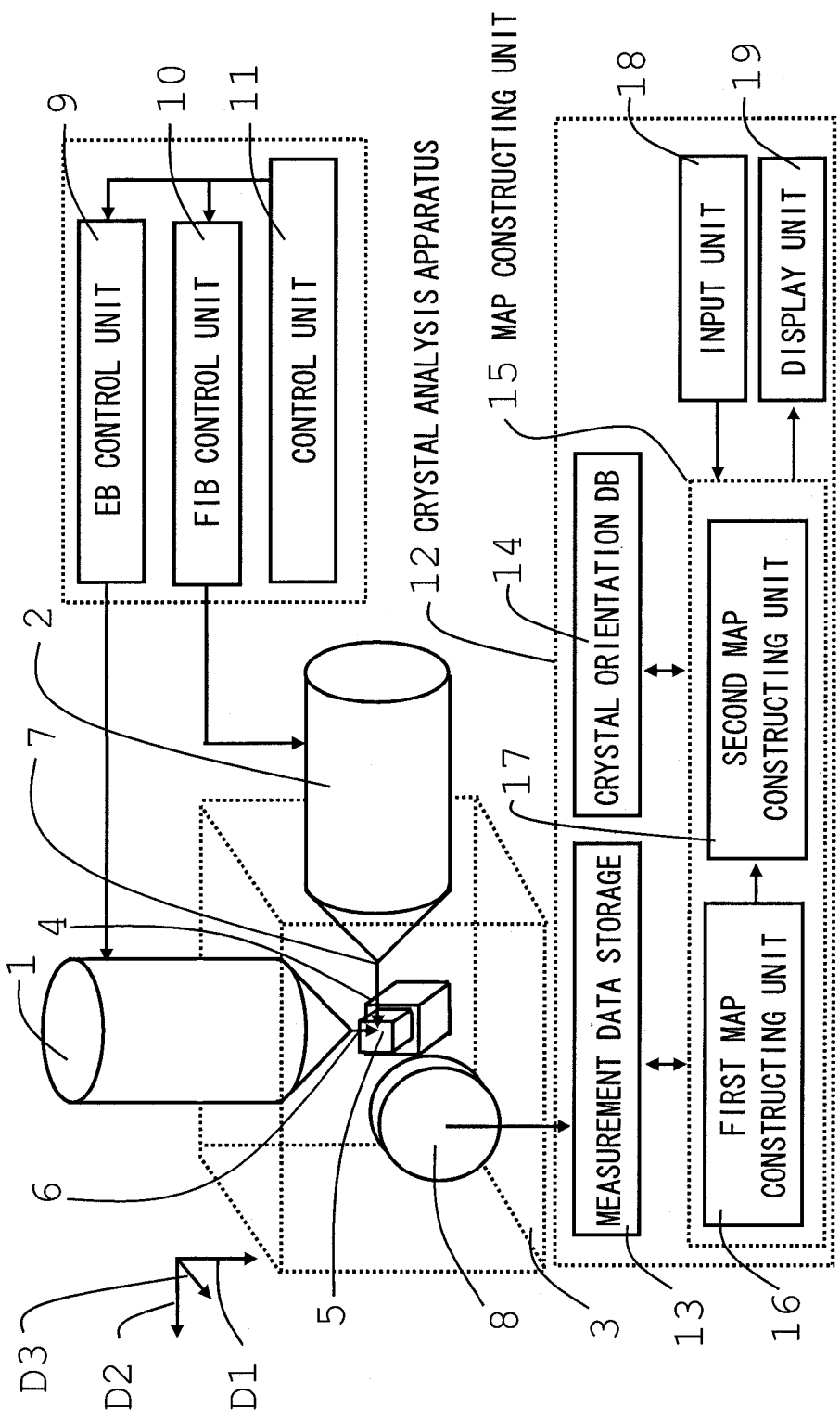
FIG. 1 is a configuration diagram of a composite charged particle beam apparatus according to an exemplary embodiment of the present invention.

A composite charged particle beam apparatus according to an exemplary embodiment of the present invention includes an EB column 1, an FIB column 2 and a sample chamber 3 as illustrated in FIG. 1. The EB column 1 and the FIB column 2 irradiate a sample 5 placed on a sample stage 4 in the sample chamber 3 with an EB 6 and an FIB 7, respectively. The sample stage 4 can be tilted so that the EB 6 is incident on the sample 5 at different angles.

The composite charged particle beam apparatus further includes an EBSP detector 8 configured to detect electrons backscattered by the sample 5 through irradiation of the EB 6.

In the composite charged particle beam apparatus, the EB irradiation axis direction D1 of the EB column 1 is orthogonal to the FIB irradiation axis direction D2 of the FIB column 2. Among the emitting directions of electrons backscattered by the sample 5, the direction orthogonal to both the directions D1 and D2 is defined as a backscattered-electron emitting direction D3. A backscattered electron detector 15 is disposed so as to detect backscattered electrons emitted in the direction D3 as well.

The EB column 1 and the FIB column 2 are arranged to have their irradiation axes orthogonally intersecting with each other on the sample 5. However, the arrangement of the EB column 1 and the FIB column 2 need not necessarily be so. Nevertheless, it is preferable to arrange these irradiation axes mutually orthogonal, because EBSP measurement can be performed through the EB 6 irradiation of cross-sections processed to be exposed by the FIB 7 without tilting the sample stage 4.

The composite charged particle beam apparatus further includes an EB control unit 9, an FIB control unit 10 and a control unit 11. The EB control unit 9 transmits an irradiation signal to the EB column 1 to control the EB column 1 to emit the EB 6. The FIB control unit 10 transmits an irradiation signal to the FIB column 2 to control the FIB column 2 to emit the FIB 7. The control unit 11 is configured to set irradiation conditions and the like for the EB 6 and the FIB 7 and to control the EB control unit 9 and the FIB control unit 10.

The composite charged particle apparatus further includes a crystal analysis apparatus 12 for performing crystal analysis based on measurement data of an EBSP detected by the EBSP detector 8.

The crystal analysis apparatus 12 includes a measurement data storage 13, a crystal orientation database (DB) 14 and a map constructing unit 15. The measurement data storage 13 stores measurement data of EBSPs detected by the EBSP detector 8. The crystal orientation DB 14 is a database that accumulates therein information of materials and crystal orientations corresponding to EBSPs.

The map constructing unit 15 reads out EBSP measurement data stored in the measurement data storage 13 and compares the measured EBSP against EBSPs stored in the crystal orientation DB 14 to identify the material and the crystal orientation corresponding to the measured EBSP. The material and the crystal orientation identified from the EBSP identify a material and a crystal orientation at an irradiation point of the EB 6 where the EBSP is measured on the sample 5. The map constructing unit then constructs a 3D crystal orientation map of the sample processed with position information of irradiation points of the EB 6 on a sample cross-section thoroughly irradiated with the EB 6, information of cutting intervals in the cross-section process, and information of materials and crystal orientations identified from EBSPs measured at irradiation points.

The map constructing unit 15 includes a first map constructing unit 16 and a second map constructing unit 17. As described in greater detail later, the first map constructing unit 16 constructs 2D crystal orientation maps of the processed cross-sections based on distribution of crystal orientations in the normal directions of the cross-sections. The second map constructing unit 17 constructs 2D crystal orientation maps of the side surfaces adjacent to the processed cross-sections of the polyhedral image of the sample based on distribution of crystal orientations in the normal directions of the side surfaces.

The crystal analysis apparatus 12 further includes an input unit 18 through which a display direction of a 3D crystal orientation map is input, and a display unit 19 for displaying the 3D crystal orientation map. The input unit 18 and the display unit 19 may be disposed separately from the crystal analysis apparatus 12. Alternatively, in place of the input unit 18 and the display unit 19 of the crystal analysis apparatus 12, input and display units connected to the control unit 11 for use in controlling may be used for inputting a display direction of the 3D crystal orientation map and displaying the 3D crystal orientation map, respectively.

Figure 2A:
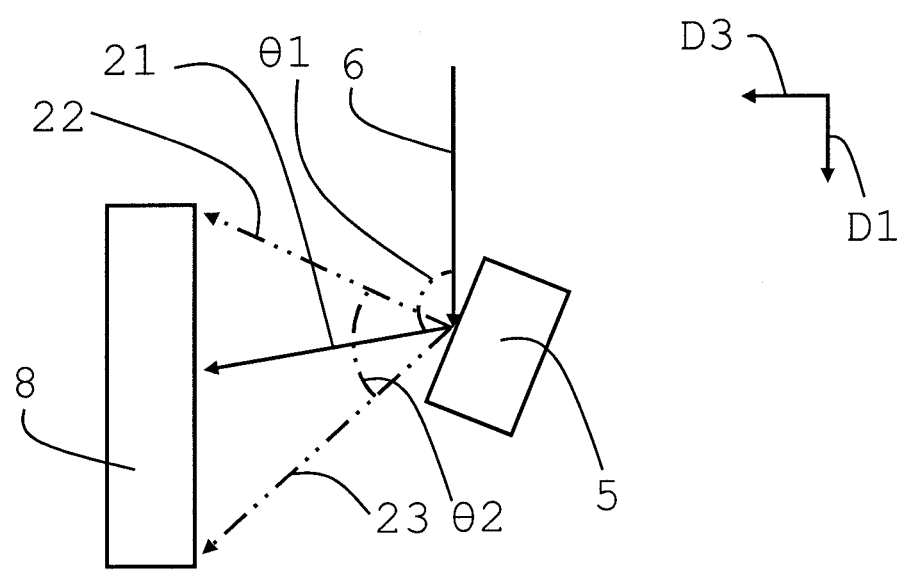
FIG. 2A is a diagram for explaining EBSP detection according to the exemplary embodiment of the present invention.

The following explains disposition of the EBSP detector 8 and a 2D crystal orientation map. FIG. 2A is a diagram for explaining EBSP detection, which is a cross-sectional view of the plane of the EB irradiation axis direction D1 and the backscattered-electron emitting direction D3. Backscattered electrons emitted in a wide range through the EB 6 irradiation are detected in a range sufficient to form an EBSP, which is the range of 70 degrees centering on a direction angled at 100 degrees to the EB 6 incident on the sample 5. In other words, the bisector direction 21 of the emission range of backscattered electrons makes an angle θ1 of 100 degrees to the EB 6 irradiation direction. The EBSP detector 8 is disposed so as to detect backscattered electrons emitted in the range of an angle θ2 of 70 degrees, centering on the bisector direction 21 of the emission range of backscattered electrons, that is, the range between a backscattered-electron emitting direction 22 and a backscattered-electron emitting direction 23. An accurate EBSP is acquired by detecting backscattered electrons emitted in this range.

Figure 2B:
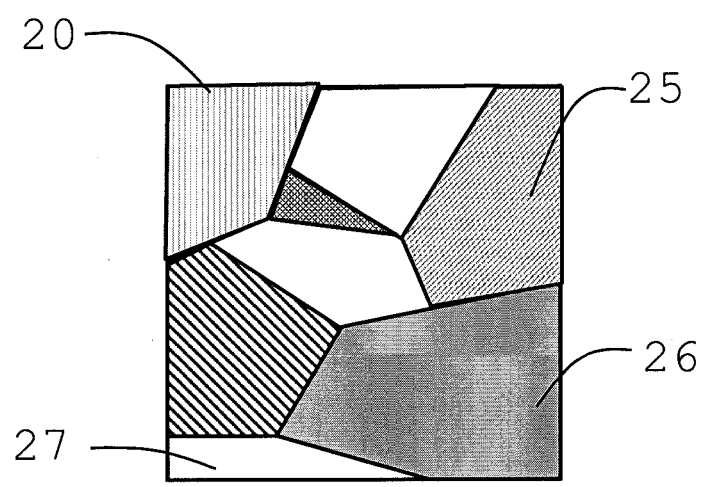
FIG. 2B is a 2D crystal orientation map of a sample according to the exemplary embodiment of the present invention.

FIG. 2B is a 2D crystal orientation map acquired by irradiating a surface 20 of the sample 5 with the EB 6. The 2D crystal orientation map is based on distribution of crystal orientations of a surface thoroughly irradiated with the EB 6.

The following explains construction of a 2D crystal orientation map. The EBSP described above is a diffraction pattern detected by the EBSP detector 8 when the EB 6 is incident at a point on the surface 20. A diffraction pattern is specific to a material and a crystal orientation. The material and the crystal orientation of a measured EBSP can thus be identified by comparing the measured EBSP against EBSPs stored in the crystal orientation DB 14, whereby the material and the crystal orientation are identified at an irradiation point of the EB 6 on the surface 20. This enables acquisition of distributions of materials and crystal orientations on the surface 20 through a thorough EB 6 irradiation.

When the sample 5 is a composite metal material made of crystal grains of a plurality of materials, distribution of crystal orientations appears on the surface 20 differently for crystal grains 25, 26, and 27 as illustrated in FIG. 2B. By allocating different colors to different materials and crystal orientations, a 2D crystal orientation map allows analysis of distribution of crystal orientations on the surface 20.

EXAMPLE

Figure 3:
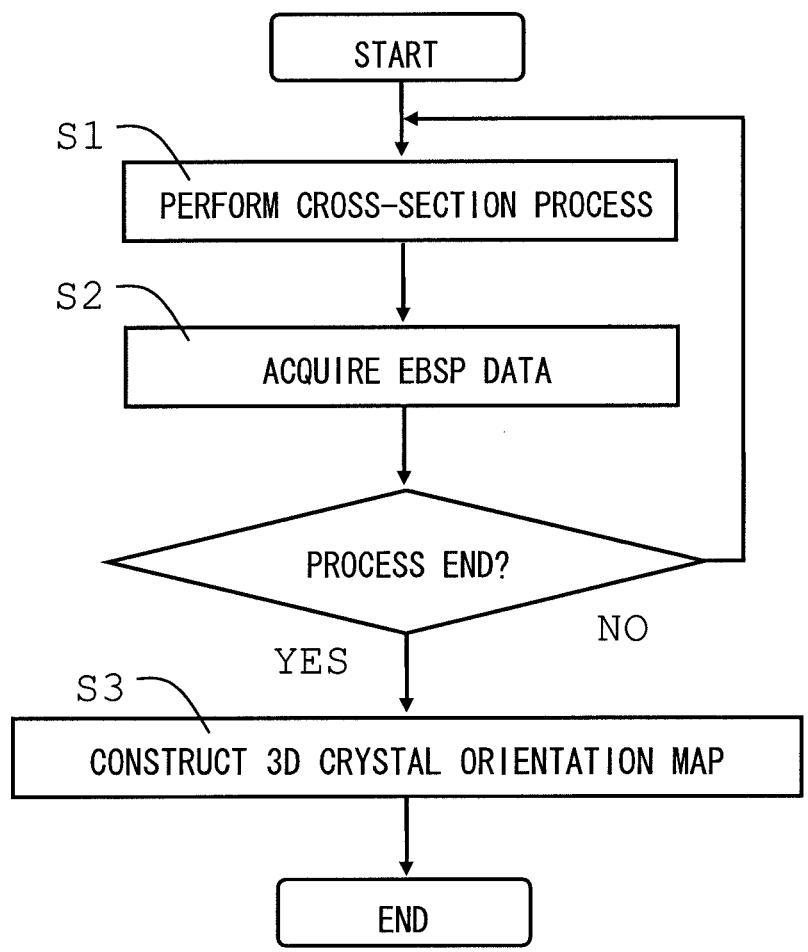
FIG. 3 is a flowchart of a crystal analysis method according to the exemplary embodiment of the present invention.

The following explains a crystal analysis method according to the present exemplary embodiment with reference to the flowchart in FIG. 3. In the crystal analysis method, EBSP measurement is performed on a part of a sample having a plurality of substantially parallel cross-sections serially processed to be exposed at prescribed intervals. From acquired EBSPs, a 3D crystal orientation map is constructed based on materials and crystal orientations of the portions whose cross-sections are processed. The map allows crystal analysis of the processed sample portions.

Figure 4A:
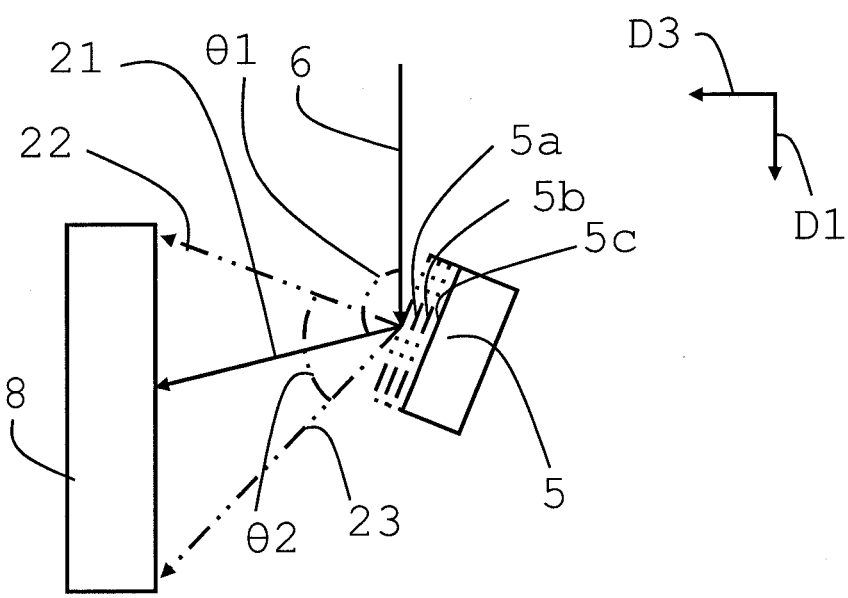
FIG. 4A is a diagram for explaining EBSP detection of a plurality of cross-sections according to the exemplary embodiment of the present invention.

The method starts with a cross-section process on a sample (S1). The cross-section process includes irradiation of the sample with the FIB 7 to etch and expose cross-sections. This etching process is a cutting process to leave the next cross-section exposed at a prescribed interval (10 nm, for example). FIG. 4A illustrates a cross-section 5*a* firstly exposed by etching.

The exposed cross-section is then thoroughly irradiated with the EB 6 to acquire EBSP data (S2). As illustrated in FIG. 4A, the cross-section 5*a* is irradiated with the EB 6 to emit backscattered electrons to be detected by the EBSP detector 8. The detected EBSP data is stored in the measurement data storage 13.

The cross-section process (S1) and the EBSP data acquisition process (S2) are repeated. The cross-section process forms cross-sections arranged substantially in parallel at prescribed intervals.

Figure 4B:
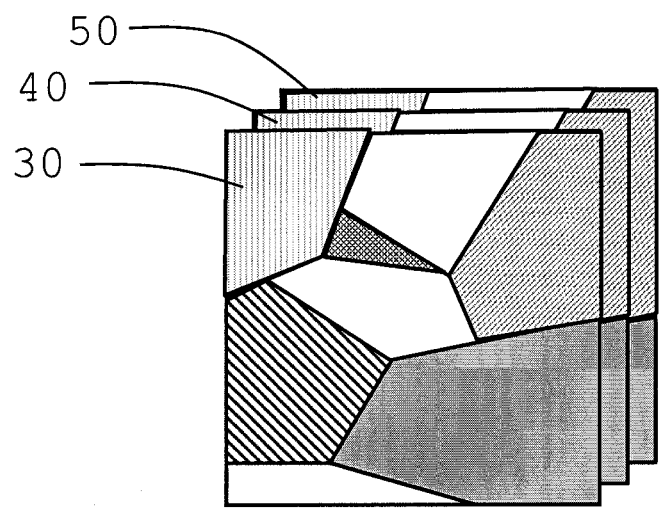
FIG. 4B is a diagram illustrating 2D crystal orientation maps of the cross-sections according to the exemplary embodiment of the present invention.

A 3D crystal orientation map is then constructed (S3). The construction of a 3D crystal orientation map includes stacking EBSP data of the cross-sections processed to be exposed. FIG. 4B illustrates 2D crystal orientation maps 30, 40 and 50, constructed with EBSP data of the cross-section 5*a* and cross-sections 5*b* and 5*c* processed to be exposed, respectively. The maps are formed with different colors allocated to different materials and crystal orientations of a plurality of crystal grains exposed on the cross-sections. The maps are arranged at cutting intervals of the cross-sections to construct a 3D crystal orientation map.

Figure 5A:
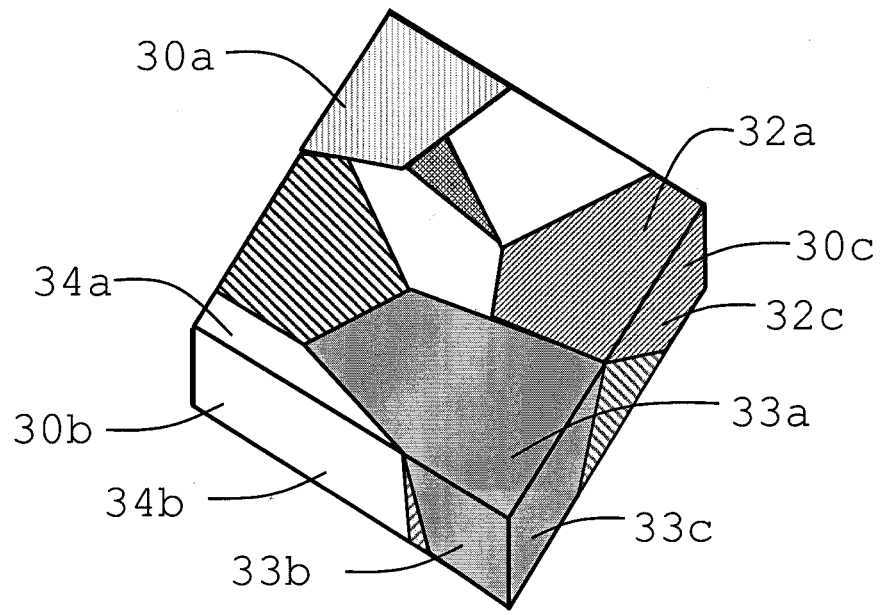
FIGS. 5A and 5B are 3D crystal orientation maps according to the exemplary embodiment of the present invention.

The following explains construction of the 3D crystal orientation map. The first map constructing unit 16 of the map constructing unit 15 of the crystal analysis apparatus 12 reads out EBSP measurement data stored in the measurement data storage 13 to compare its measured EBSP against EBSPs stored in the crystal orientation DB 14, thereby identifying the material and the crystal orientation of the measured EBSP. The 3D crystal orientation map as illustrated in FIG. 5A is then constructed from three pieces of information. The information includes: position information of irradiation points of the EB 6 on the cross-sections thoroughly irradiated with the EB 6; information of cutting intervals in the cross-section process, which is information of intervals between the cross-sections 5*a*, 5*b*, and 5*c*; and information of the materials and the crystal orientations identified from EBSPs measured at the irradiation points.

The 3D crystal orientation map represents distributions of materials and crystal orientations, and displays materials and crystal orientations in different colors.

The 3D crystal orientation map is composed of: a 2D crystal orientation map 30*a* of the cross-section 5*a*; a 2D crystal orientation map 30*b* of a first side surface; and a 2D crystal orientation map 30*c* of a second side surface. The 2D crystal orientation map 30*a* of the cross-section 5*a* displays crystal grains 32*a*, 33*a*, and 34*a* of the cross-section 5*a*. The 2D crystal orientation map 30*b* of the first side surface displays crystal grains 33*b* and 34*b* of the first side surface. The 2D crystal orientation map 30*c* of the second side surface displays crystal grains 32*c* and 33*c* of the second side surface.

Colors on the side surfaces are based on information of crystal grains on the cross-sections. Crystal grains adjacent to the 2D crystal orientation map 30*a* of the cross-section 5*a* are given colors indicating crystal orientations on the 2D crystal orientation map 30*a* of the cross-section 5*a*. In other words, side surfaces adjacent to the cross-section 5*a* display crystal orientations in the normal direction of the cross-section 5*a* for crystal grains on the side surfaces adjacent to crystal grains on the cross-section 5*a*. When correctly displayed, however, the crystal orientation of a crystal grain should differ between on the cross-section 5*a* and on the side surfaces. The second map constructing unit 17 thus constructs a 3D crystal orientation map displaying side surfaces of crystal orientations in the normal directions of the side surfaces based on information of the 3D crystal orientation map constructed by the first map constructing unit 16 and information of crystal orientations of EBSPs accumulated in the crystal orientation DB 14. This configuration allows crystal orientations to be correctly displayed on the side surfaces.

Figure 5B:
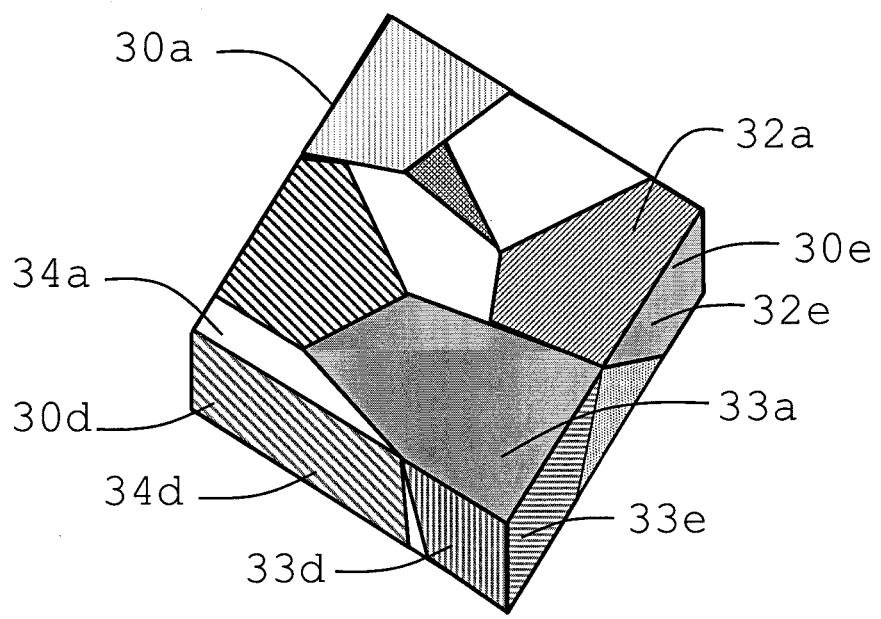

FIG. 5B illustrates the 3D crystal orientation map constructed by the second map constructing unit 17. The 3D crystal orientation map is composed of: the 2D crystal orientation map 30a of the cross-section 5a; a 2D crystal orientation map 30d of the first side surface; and a 2D crystal orientation map 30e of the second side surface. The 2D crystal orientation map 30d of the first side surface and the 2D crystal orientation map 30e of the second side surface in FIG. 5B have crystal orientations different from those of the 2D crystal orientation map 30b of the first side surface and the 2D crystal orientation map 30c of the second side surface, respectively, in FIG. 5A.

For example, in FIG. 5A, the same color indicating the same crystal orientation is allocated to the crystal grain 33a on the 2D crystal orientation map 30a of the cross-section 5a, the crystal grain 33b of the 2D crystal orientation map 30b of the first side surface, and the crystal grain 33c of the 2D crystal orientation map 30c of the second side surface. On the other hand, in FIG. 5B, different colors indicating different crystal orientations from that of the crystal grain 33a are allocated to a crystal grain 33d of the 2D crystal orientation map 30d of the first side surface and a crystal grain 33e of the 2D crystal orientation map 30e of the second side surface. When the crystal grains are viewed in different directions, specifically in the normal directions of the cross-section 5a and the first side surface, different crystal orientations are observed in the respective directions. When the crystal grain 33a has the (001) orientation of iron, specifically the crystal grains 33d and 33e have the (100) orientation and the (010) orientation of iron, respectively. The 3D crystal orientation map in FIG. 5B thus displays correct crystal orientations on the side surfaces.

FIGS. 5A and 5B illustrate the cross-section 5a as a front face, but the 3D crystal orientation map may be set to display, for example, the first side surface as a front face.

Figure 6:
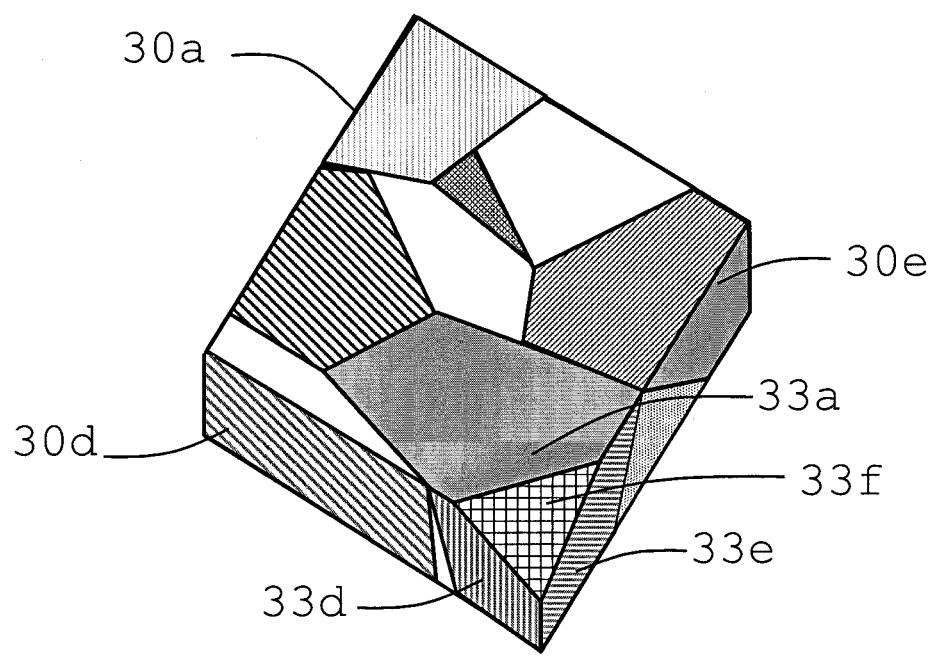
FIG. 6 is a 3D crystal orientation map according to the exemplary embodiment of the present invention.

The second map constructing unit 17 is able to display a crystal orientation map of a cross-section obtained by cutting the hexahedron of the 3D crystal orientation map at a desired angle. FIG. 6 illustrates a 3D crystal orientation map obtained by cutting off a portion of the 3D crystal orientation map in FIG. 5B and displaying the formed cross-section, in which a crystal grain 33f is displayed. Specifically the crystal grain 33f has the (111) orientation of iron. In this manner, a 3D crystal orientation map can be cut to expose any desired face and display correct crystal orientations on the exposed face.

In the above-described exemplary embodiment, the map constructing unit 15 includes the first map constructing unit 16 and the second map constructing unit 17. However, the present invention is not limited to this configuration as long as the map constructing unit 15 constructs a 3D crystal orientation map indicating crystal orientations in the normal directions of a plurality of faces of a polyhedral image of a sample.

A 3D crystal orientation map constructed as described above to display correct crystal orientations of a sample allows accurate analysis of the crystal structure of the sample.

What is claimed is:

1. A crystal analysis apparatus comprising:
a measurement data storage configured to store electron back-scattering pattern (EBSP) data measured at electron beam irradiation points on a plurality of cross-sections of a sample formed substantially in parallel at prescribed intervals;
a crystal orientation database configured to accumulate therein information of crystal orientations corresponding to EBSPs; and
a map constructing unit configured to construct a three-dimensional crystal orientation map based on distribution of crystal orientations in normal directions of a plurality of faces of a polyhedral image having the cross-sections arranged at the prescribed intervals by reading out the crystal orientations in the normal directions of the faces from the crystal orientation database on the basis of the EBSP data stored in the measurement data storage.

2. The crystal analysis apparatus according to claim 1, wherein the faces of the polyhedral image comprise a plurality of crystal grains with different crystal orientations.

3. The crystal analysis apparatus according to claim 1, wherein the faces of the polyhedral image comprise internal faces tilted with respect to side surfaces of the polyhedral image.

4. The crystal analysis apparatus according to claim 1, wherein the map constructing unit comprises:
a first map constructing unit configured to construct a first two-dimensional crystal orientation map based on distribution of crystal orientations in a normal direction of a first face of the polyhedral image; and
a second map constructing unit configured to construct a second two-dimensional crystal orientation map based on distribution of crystal orientations in a normal direction of a second face adjacent to the first face.

5. The crystal analysis apparatus according to claim 1, further comprising:
an input unit for designating a display direction of the three-dimensional crystal orientation map.

6. A composite charged particle beam apparatus comprising:
the crystal analysis apparatus according to claim 1;
a focused ion beam column configured to emit a focused ion beam to form the cross-sections;
an electron beam column configured to irradiate the cross-sections with an electron beam; and
an EBSP detector configured to detect an EBSP at an irradiation point of the electron beam on the cross-sections.

7. A crystal analysis method comprising:
(A) forming a cross-section on a sample by irradiating the sample with a focused ion beam;
(B) detecting an electron back-scattering pattern (EBSP) at an electron beam irradiation point on the cross-section by irradiating the cross-section with an electron beam;
(C) repeating (A) and (B) to acquire EBSPs of a plurality of cross-sections arranged substantially in parallel at prescribed intervals to perform crystal analysis of the sample; and
(D) constructing a three-dimensional crystal orientation map based on distribution of crystal orientations in normal directions of a plurality of faces of a polyhedral image having the cross-sections arranged at the prescribed intervals on the basis of the EBSP data.

8. The crystal analysis method according to claim 7, wherein the faces of the polyhedral image include internal faces tilted with respect to side surfaces of the polyhedral image.

9. The crystal analysis method according to claim 7, wherein the constructing of a three-dimensional crystal orientation map comprises:
constructing a two-dimensional distribution of crystal orientations in a normal direction of a first face of the polyhedral image; and
constructing a two-dimensional distribution of crystal orientations in a normal direction of a second face adjacent to the first face.

10. The crystal analysis method according to claim 7, further comprising:
 designating a display direction of the three-dimensional crystal orientation map; and
 displaying the three-dimensional crystal orientation map in the designated display direction.

\* \* \* \* \*